(12) United States Patent
Smith et al.

(10) Patent No.: US 7,846,083 B2
(45) Date of Patent: Dec. 7, 2010

(54) LEFT VENTRICLE ASSIST DEVICE (LVAD)

(75) Inventors: Robert M. Smith, Grosse Ile, MI (US); Roger W. Snyder, New Braunfels, TX (US); Adrian Kantrowitz, Auburn Hills, MI (US); Allen B. Kantrowitz, Williamstown, MA (US)

(73) Assignee: L-VAD Technology, Inc.

( * ) Notice: Subject to any disclaimer, the term of this patent is extended or adjusted under 35 U.S.C. 154(b) by 661 days.

(21) Appl. No.: 11/679,487

(22) Filed: Feb. 27, 2007

(65) Prior Publication Data

US 2007/0265490 A1  Nov. 15, 2007

Related U.S. Application Data

(60) Provisional application No. 60/778,170, filed on Feb. 27, 2006.

(51) Int. Cl.
*A61N 1/00* (2006.01)

(52) U.S. Cl. ......................................................... 600/16

(58) Field of Classification Search .................... 600/16, 600/17, 18; 623/3.1, 3.16, 3.21, 3.26
See application file for complete search history.

(56) References Cited

U.S. PATENT DOCUMENTS

| | | | |
|---|---|---|---|
| 4,630,597 A | 12/1986 | Kantrowitz et al. | |
| 5,282,849 A | 2/1994 | Koiff et al. | |
| 5,290,227 A | 3/1994 | Pasque | |
| 6,045,496 A | 4/2000 | Pacella et al. | |
| 6,136,025 A | 10/2000 | Barbut et al. | |
| 6,210,318 B1 | 4/2001 | Lederman | |
| 6,471,633 B1 | 10/2002 | Freed | |
| 6,511,412 B1 * | 1/2003 | Freed et al. | 600/17 |
| 6,579,223 B2 | 6/2003 | Palmer | |
| 2004/0152945 A1 * | 8/2004 | Kantrowitz et al. | 600/18 |

* cited by examiner

*Primary Examiner*—George Manuel
*Assistant Examiner*—Shubatra Narayanaswamy
(74) *Attorney, Agent, or Firm*—Gifford, Krass, Sprinkle, Anderson & Citkowski, P.C.

(57) ABSTRACT

A pump has an elongated shell with a generally elliptical shape, an outer convex surface and an inner concave surface. A peripheral side edge located between the inner and outer surfaces terminates in a bead edge. A flexible airtight membrane has a membrane edge bonded to the outer shell surface adjacent to the bead edge. Preforming the membrane edge looped with a maximum linear span of curvature that is greater than a maximal transverse linear extent of the bead edge, membrane operational wear during inflation and deflation cycles is reduced in the region around the bead edge. A process of forming a blood pump with a membrane preform is also provided.

16 Claims, 13 Drawing Sheets

LEFT VENTRICLE ASSIST DEVICE (LVAD)

CROSS-REFERENCE TO RELATED APPLICATIONS

This application claims priority of U.S. Provisional Patent Application Ser. No. 60/778,170 filed Feb. 27, 2006, which is incorporated herein by reference.

FIELD OF THE INVENTION

The present invention relates generally to a cardiac assist device, and in particular to a left ventricular assist device ("LVAD") intended to work in series with a patient heart to augment tissue perfusion.

BACKGROUND OF THE INVENTION

For purposes of background, the disclosures of the following patent documents are hereby incorporated by reference in their entirety: U.S. Pat. Nos. 4,051,840; 4,630,597; 4,692,148; 4,733,652; 4,809,681; 5,169,379; 5,761,019; 5,833,619; 5,904,666; 6,042,532; 6,132,363; 6,471,633; 6,511,412; 6,735,532; and U.S. patent application Ser. Nos. 10/746,543; 10/770,269; 10/865,965; 11/178,969; and 60/709,323.

The scarcity of human hearts available for transplant, as well as the logistics necessary to undertake heart transplant surgery, make an implantable cardiac assist device the only viable option for many heart patients. An aortic blood pump, for example, can be permanently surgically implanted in the wall of the aorta to augment the pumping action of the heart.

A known aortic blood pump includes a flexible bladder to be inflated and deflated in a predetermined synchronous pattern with respect to the diastole and systole of the patient to elevate aortic blood pressure immediately after aortic valve closure. Inflation and deflation of the bladder is accomplished by means of a supply tube connected to the bladder and to a percutaneous access device ("PAD"). The PAD is permanently surgically implanted in a patient's body to provide a through-the-skin coupling for connecting the supply tube to an extra-corporeal fluid pressure source. Electrical leads from electrodes implanted in the myocardium are likewise brought out through the skin by means of the PAD, The "R" wave of the electrocardiograph is used to control the fluid pressure source to inflate and deflate the inflatable chamber in a predetermined synchronous relationship with the heart action.

The aortic blood pump acts to assist or augment the function of the left ventricle and is typically restricted to use in patients who have some functioning myocardium. The aortic blood pump does not need to be operated all the time, and in fact, can be operated periodically on a scheduled on-time, off-time regimen, or on an as-needed basis. Typically, the patient can be at least temporarily independent of the device for periods of one to four hours or more, depending on their heart function and level of activity. The general structure of known aortic blood pumps is a semi-rigid concave shell, and a flexible membrane that is integrally bonded to the outer surface of the shell, forming an inflatable and deflatable chamber. A fabric layer is then bonded over the exterior surface of the shell that projects clear of the shell forming a suture flange. These blood pumps have been tested and demonstrated to last a few million cycles. None of the known blood pumps disclose or suggest that any modification can be made to the geometry of the shell and membrane to increase the durability of the pump, much less what such modification would be.

A known dynamic aortic patch has an elongate bladder having a semi-rigid shell with walls of uniform thickness and a relatively thicker peripheral edge and a flexible, relatively thin membrane defining an inflatable chamber. At least one passage extends through the shell defining an opening in the inner surface of the shell. The flexible membrane is continuously bonded to the shell adjacent the peripheral side edge to define the enclosed inflatable chamber in communication with the passage. The membrane may have a reduced waist portion, defining a membrane tension zone adjacent to the opening of the passage into the chamber to prevent occluding the opening to the pneumatic supply while deflating the chamber. An outer fabric layer can be bonded to the outer side of the shell of the aortic blood pump, and present a freely projecting peripheral edge to provide a suture flange for suturing the aortic blood pump in place within an incision in the aorta.

Known aortic blood pumps use an inflatable bladder and an envelope. The envelope is sutured to the aorta and then the bladder is placed inside the envelope. Although this design successfully augments the blood pumping capacity of the heart, it has two major disadvantages. First, fluid may accumulate inside the envelope, between the envelope and the inflatable bladder. This accumulation of static fluid within the body commonly leads to infection. Second, due to the geometry of the bladder, the volume of blood displaced by the device is limited, and has been determined to be insufficient.

Experience with patients has shown that it is relatively easy to construct a pump that will last a few million inflation-deflation cycles (on the order of weeks). However, it is very difficult to design, reproducibly manufacture, and implant a pump that will last for at least two years (on the order of a hundred million of inflation-deflation cycles, or more) without membrane failure.

The top surface of the pump's shell can be overlaid with a non-tissue adhesive substance, such as silicone, to prevent scar tissue from adhering to the back of the pump and to allow the pump to be explanted later. But clinical experience has shown that even this improved design may last less than the two-year target in a patient.

Known blood pumps have a suture ring placement that constrains the movement of the blood pump during each inflation-deflation cycle. In these designs, the suture ring is located closely adjacent to the shell bead, in a location outside of the periphery of the shell, and at approximately the same height (measured as the axial distance from the centerline of the aorta) as that of the bead. When the implantation wound heals, the suture line itself, as well as the scar tissue that grows into the suture line, constrain the movement of the shell during each inflation-deflation cycle. This occurrence results in effectively stiffening the shell near the region where it interacts with the membrane, thus forcing the membrane to absorb all of the stress during the inflation-deflation cycles.

The hose barb provides the connection between the internal conduit and the blood pump. Known blood pumps have hose barbs that are glued into place to the back of the shell of the blood pump. This design can be improved to increase the strength of the hose barb's attachment to the shell.

As seen in FIG. 11, the shells of prior art blood pumps are relatively flat across their length, other than slightly turning downwards at the longitudinal ends, and have relatively thin walls of uniform thickness with slightly thicker peripheral edges. However, despite the simplified drawings of aorta in FIGS. 2, 3, and 11, the human aorta is not a straight circular cylinder. Rather, it has a complex three-dimensional shape, sometimes described as a "twisted question mark." Accordingly, the known flat blood pumps are not well configured to fit to a typical human aorta, and there is a need in the art for a blood pump having a contour that generally matches the contour of a typical human aorta. Further, because of their general cylindrical configuration and relatively thin walls, the permanent deformation of these pumps during surgical implantation into the non-cylindrical aorta can affect their durability.

Thus, although the art discloses the basic concept of an "in-series" mechanical ventricle assist device (blood pump), having a semi-rigid shell, and a flexible membrane, nothing in the art teaches or suggests how to construct a device that will be durable enough to survive inflation-deflation cycles for the number of years desired. To the contrary, clinical experience has shown that the known blood pumps generally last less than the two-year target. Thus, there remains a need in the art for a blood pump design providing increased durability.

SUMMARY OF THE INVENTION

A blood pump for placement in an incision in an aorta is provided that after placement contacts blood passing through the aorta. The pump inflates and deflates in order to provide left ventricular assistance. The pump has an elongated shell with a generally elliptical shape, an outer convex surface and an inner concave surface. A peripheral side edge located between the inner and outer surfaces terminates in a bead edge. A passage is provided through the shell to provide fluid communication between the outer surface and inner surface. A flexible airtight membrane has a membrane edge bonded to the outer shell surface adjacent to the bead edge to form an enclosed internal chamber in fluid communication with the passage. Preforming the membrane edge looped with a maximum linear span of curvature that is greater than a maximal transverse linear extent of the bead edge, membrane operational wear during inflation and deflation cycles is reduced in the region around the bead edge.

A process of forming a blood pump with a membrane preform is provided that includes placing an airtight membrane around a platen having a platen edge bead with a curvature of maximal transverse linear extent and a platen footprint substantially identical to a footprint of the blood pump shell. By heat setting the membrane, a looped membrane edge is formed as complementary to the curvature of the platen edge bead to yield a membrane preform. The membrane preform is secured to the outer surface of the shell having a bead edge of maximum linear extent less than the curvature of the looped membrane edge.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE PREFERRED EMBODIMENTS

Figure 1:
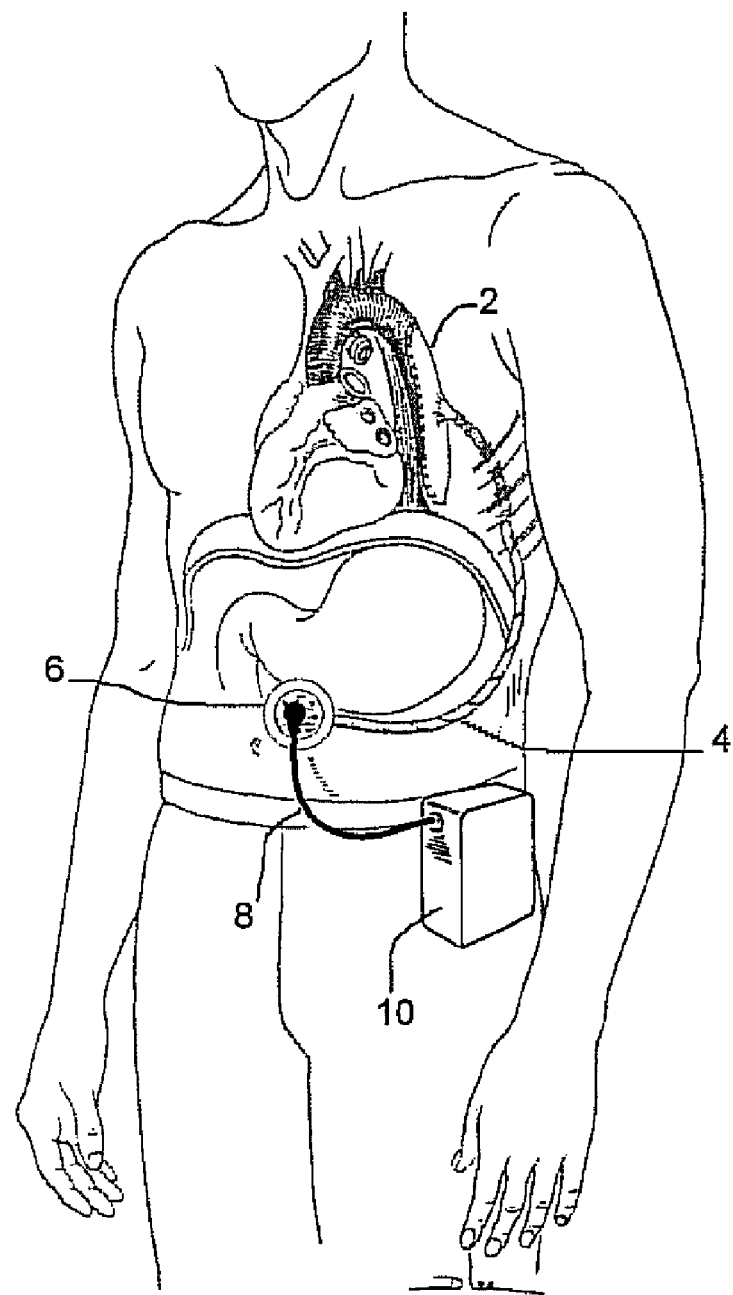
FIG. 1 is a schematic perspective view of the major components of an LVAD system, as known in the art, implanted in a patient.

The present invention has utility as an implantable cardiac assist device. Through a modification of shell structure to include an enlarged bead edge relative to the shell wall the operational stability of the pump is enhanced.

For convenience, the same or equivalent elements in the various embodiments of the invention illustrated in the drawings have been identified with the same reference numerals. Further, in the description that follows, any reference to either orientation or direction is intended primarily for the convenience of description and is not intended in any way to limit the scope of the present invention thereto.

A basic known LVAD system, as shown in FIG. 1, consists of the blood pump 2, an inflatable bladder sutured into the wall of the aorta; an internal conduit 4 connecting the blood pump to the percutaneous access device ("PAD"); the PAD 6, a through-the-skin port that permits power, electrical signals and fluid (typically air) to pass between the drive unit and blood pump; and the external drive unit 10, a device powering and controlling the blood pump. The PAD 6 allows the implanted blood pump 2 to be operatively connected to or disconnected from the external drive unit 10. To inflate the blood pump 2, pressurized air is supplied from the drive unit compressor (not shown). The air flows from the compressor via an interconnect tube through a valve manifold in the drive unit 10 to an external drive line 8 running to the PAD 6 and then through the implanted internal conduit 4 to the blood pump 2. Alternatively, an isolation chamber, separating the pressure (or vacuum) source from the air flowing to the pump, can be used to isolate the subcutaneous portion of the pneumatic circuit from the supercutaneous portion.

Figure 2:
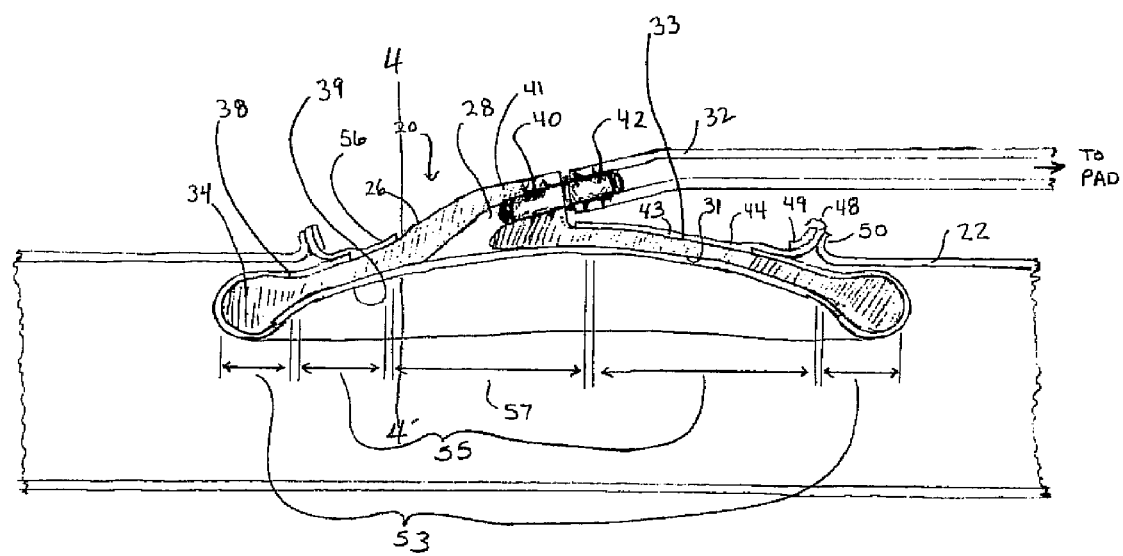
FIG. 2 is a schematic view of a longitudinal cross-sectional view of a blood pump in a deflated state.
Figure 3:
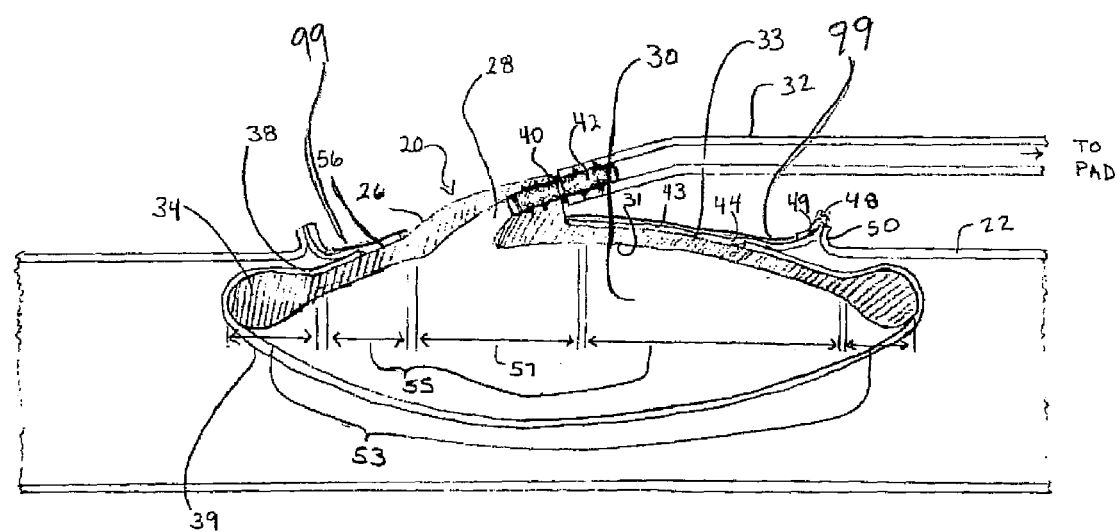
FIG. 3 is a schematic view of a longitudinal cross-sectional view of a blood pump in an inflated state.

As seen in the longitudinal cross-sectional views of FIGS. 2 and 3, the improved blood pump 20 of the present invention is implanted within the wall of the thoracic aorta 22. The membrane 38 of the blood pump 20 is illustrated during deflation in FIG. 2 and during inflation in FIG. 3. To implant the device, a surgeon makes a longitudinal incision through the wall of the aorta, usually downward from a location just below the subclavian artery, and the device is placed within the incision and sewn firmly in position by sutures (not shown) passing through a projecting suture ring flange 48.

Figure 8:
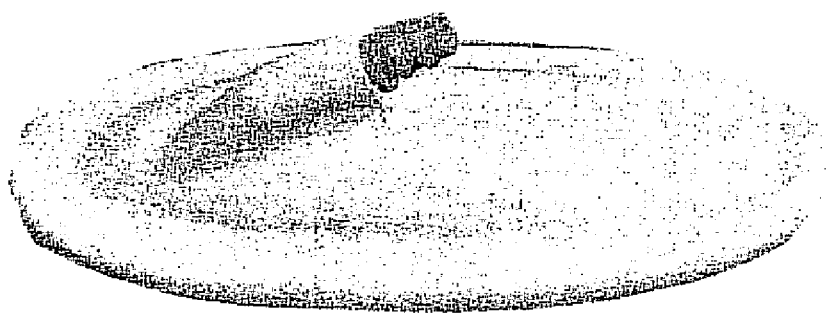
FIG. 8 is a perspective view of a blood pump shell, including a hose barb.

The outer side of the blood pump 20, as implanted, is a relatively thick, semi-rigid shell 26, which is molded from a suitable biocompatible material, such as urethane. As best seen in FIG. 8, the shell 26 is of an elongate elliptical shape, with its upper or outer surface 33 being convex in both its longitudinal and transverse extents. The lower or inner surface 31 of the shell 26 is concave in its longitudinal and transverse extents, as seen in FIGS. 2-5.

The shell 26 can be considered as having three regions: the spine region 57, the wall region 55, and the bead region 53. The spine region 57 of the shell 26 is the relatively thick area of the shell that forms the housing 41 around the hose barb 40, together with the area immediately surrounding the housing 41. A passage 28 extends though the shell 26 to place the interior volume 30 of the blood pump 20 in fluid communication with the internal conduit 32 of the blood pump 20.

The wall region 55 of the shell 26 is preferably thinner than the spine region 57 and extends out from the spine region 57 as seen in FIGS. 2 and 3.

The bead region 53 of the shell has a bead 34, and is thicker than the wall region 55. The peripheral side edge of the shell 26 is smoothly rounded around its circumference, as best seen in FIGS. 2 and 3, and around its cross section, as best seen in FIGS. 2-4, such that the bead 34, which runs along the periphery of the shell 26, is itself smoothly rounded throughout its entire extent, circumferentially around the elliptical shell, and also around its cross section. The shape of the bead 34 lessens local flexing stress, particularly when the membrane 38 is taut around the edge during the pump deflation cycle.

The membrane 38 is flexible, thin walled and bonded to the outer surface 33 of the shell 26. The membrane 38 is preferably not adhered to the bead 34 or inner surface 31 of the shell 26. Known solvation bonding techniques such as chlorinated solvent welding of polymers result in the membrane 38 and the shell 26 becoming what is in effect a unitary structure, but for purposes of explanation, the membrane 38 and the shell 26 are drawn in FIGS. 2 and 3 as separate components.

The outer surface 39 of the membrane 38 which, when implanted, interfaces with the blood in the aorta is preferably provided with fibrils, forming a textured surface similar to a flocking, to promote cellular adhesion in forming a pseudo-intima on the outer surface 39 of the membrane 38.

Figure 10:
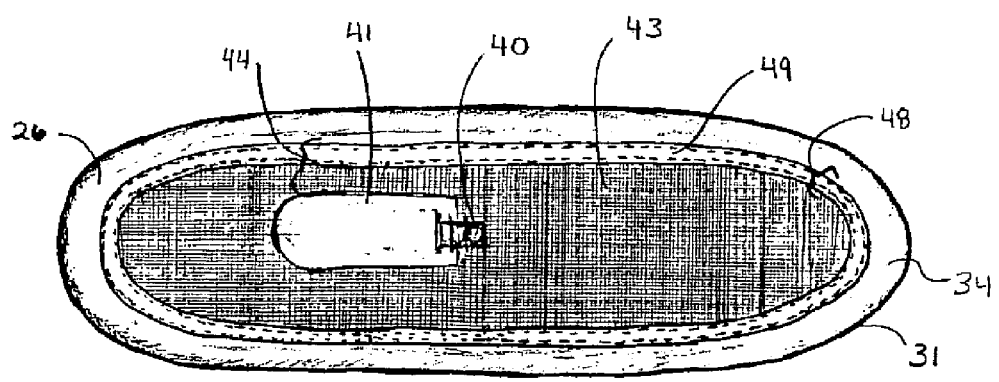
FIG. 10 is a perspective view of a blood pump shell, including a hose barb and a suture ring.

A piece of sheet material 43 is attached to the outer surface 33 of the shell 26. As indicated in FIGS. 2 and 3, the periphery of the material 43 is preferably not attached to the outer surface 33 of the shell 26 and projects freely from the shell 26 to create a flange 48. An additional material strip 49, such as a pledget strip, is secured to the flange 48 by for example stitching, to provide a suture ring 44 for implanting the device in an incision in the aorta, as best shown in FIGS. 2, 3 and 10. The strip 49 preferably has a fibrous surface allowing body tissues to migrate into, and mechanically interweaving with the strip 49, to augment the sealing action initially established by the surgical implantation sutures (not shown) between the flange 48 of the suture ring 44 and the wall 50 of the aorta 22. The sheet material 43 and strip 49 are made of various appropriate materials, such as polyester, which are commercially available and have been certified for use in implanted devices.

A number of modifications are optionally made to increase the durability of the blood pump by reducing the physical wear and stress on the membrane. The membrane failure of prior art designs is understood to have often been caused by microperforations due to membrane deformation, or "creasing," during inflation-deflation cycles.

Figure 9:
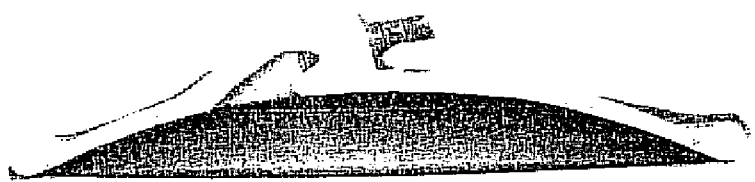
FIG. 9 is a longitudinal cross-sectional view of a blood pump shell, including a hose barb.

A blood pump is provided that has a contour that generally matches that of a typical human aorta. As seen in FIGS. 2, 3, and 9, the blood pump shell has a pronounced, continuous curve across its entire longitudinal extent. The interior curve of the shell as seen in FIG. 9 corresponds to the curvature of the aorta at the point of blood pump implantation. This curvature allows the pump to match the contour of a typical human aorta better than prior art pumps.

Figure 4A:
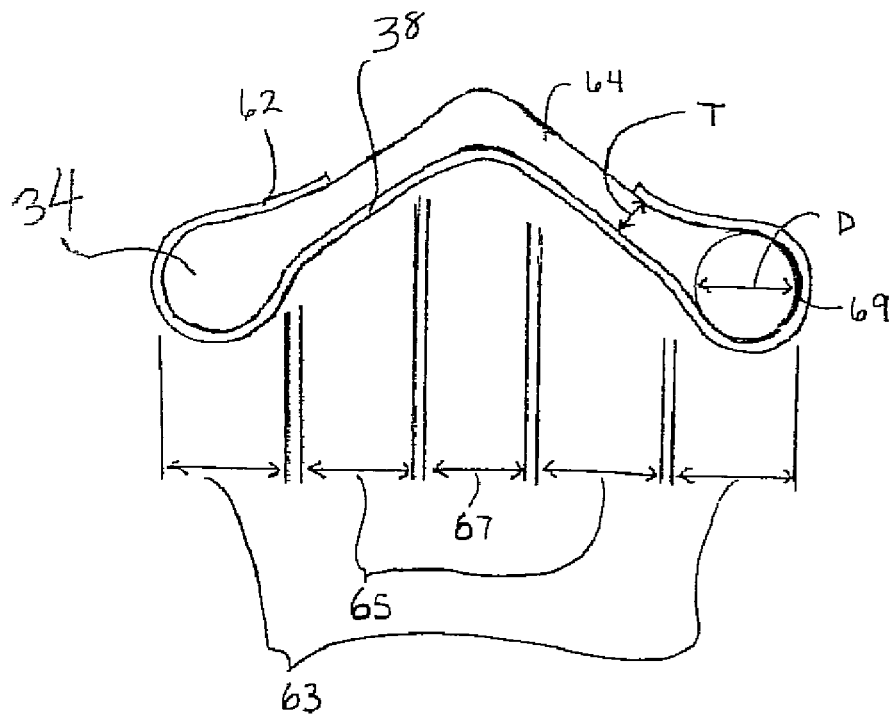
FIG. 4 is a schematic view of a transverse planar cross-sectional view along line 4-4' of the pump shown in FIG. 2 in a deflated state.
Figure 4B:
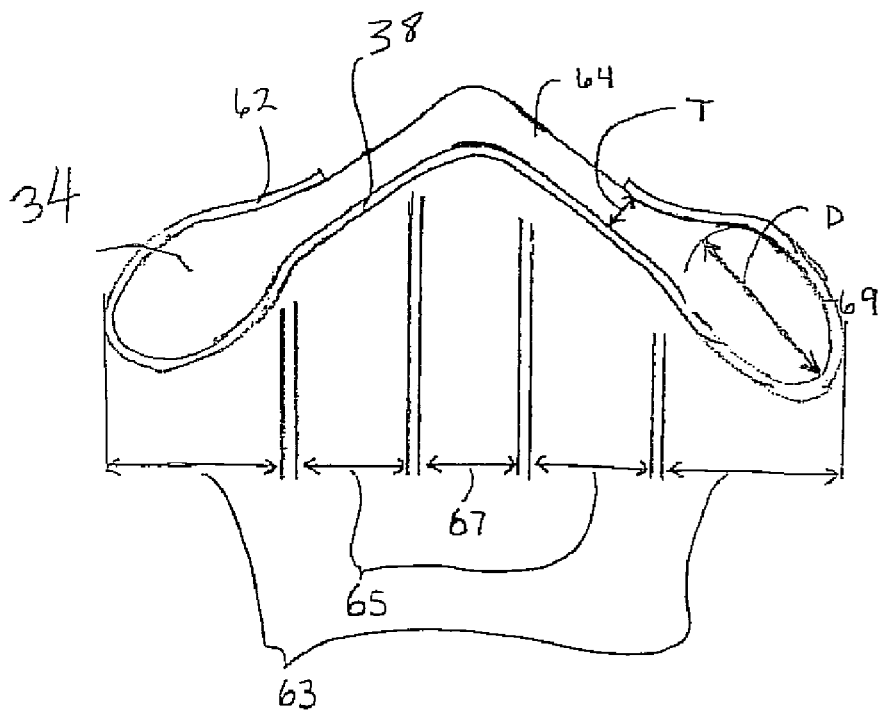

An inventive blood pump is provided with a large-diameter bead relative to the adjoining wall region of a pump shell to reduce the stress on the membrane during the cyclical operation of the pump. The large-diameter bead reduces stresses on the parts of the membrane coming in contact with the bead during the deflation cycle, while still being sufficiently flexible to be twisted and flexed during surgical implantation. Such properties are derived by varying the bead diameter relative to the shell thickness. As seen in the transverse planar cross-sectional view of the pump in FIG. 4A, the bead 34 has a membrane-contacting region 69 which contacts the membrane 38 when the pump is deflated. The portions of the pump 20 not in the plane of the transverse cut are not shown for visual clarity. As seen in FIG. 4A, the transverse wall region 65 of the shell 26 has a thickness T adjacent to the bead region 63. A transverse spine region 67 is also defined. Preferably, the thickness of regions 55-65, 53-63 and 57-67 are substantially equivalent. In order to further reduce localized stresses on the membrane 38 during the deflation cycle, the maximal linear extent D of the bead 34 at the membrane-contacting region 69 is preferably between about 110% to about 700% of T. In other words, $\approx 1.1\ T \leq D \leq \approx 7\ T$. More preferably, D is between about 200% to about 600% of T. In other words, $\approx 2\ T \leq D \leq \approx 6\ T$. Even more preferably, D is between about 400% to about 500% of T. In other words, $\approx 4\ T \leq D \leq \approx 5\ T$. It is appreciated that while the bead 34 is depicted as spherical in cross section resulting in the maximal linear extent D corresponding to the diameter of the bead and that the bead is readily formed in a variety of shapes devoid of a sharp corner corresponding to a mathematical derivative singularity. An alternate bead shape in cross section is ellipsoidal, as shown in FIG. 4B.

In absolute dimensions, mathematical modeling/simulation and laboratory testing was conducted on a pump with the following approximate dimensions:

Overall length=130 mm
Overall width=38 mm
Wall thickness in wall region=2 mm

The testing indicated that on this pump, a bead diameter of approximately 7.0 mm advantageously reduced localized stress on the membrane, while still providing a shell with sufficient flexibility for purposes of implantation, and sufficient rigidity to hold its shape as required during implantation and use in vitro.

Figure 5:
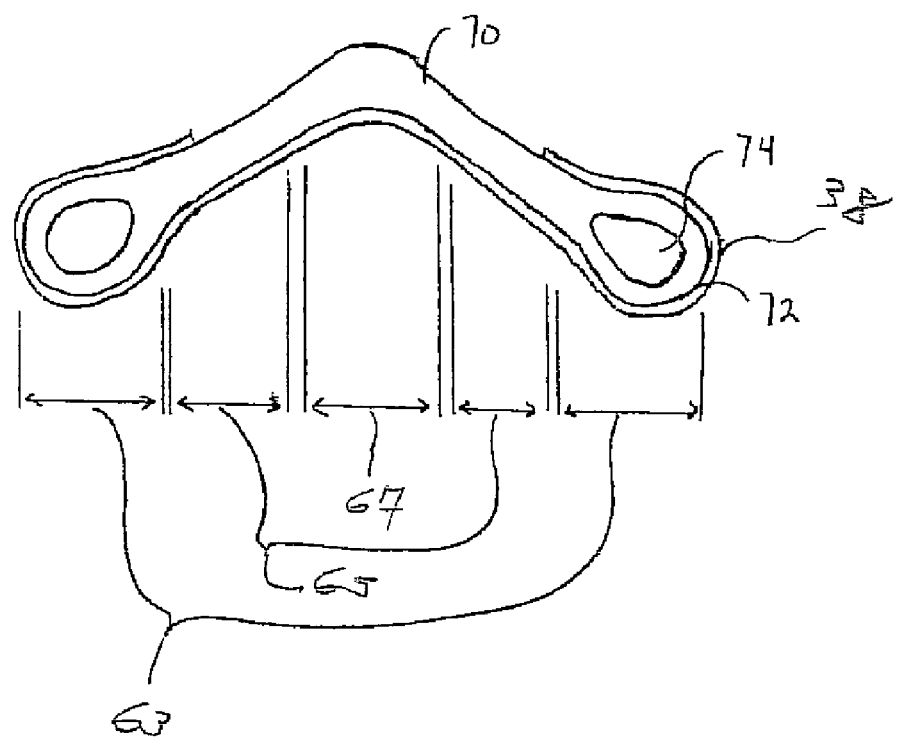
FIG. 5 is a schematic view of a transverse planar cross-sectional view of a blood pump in a deflated state, in an embodiment with a shell having a hollow bead.

An inventive shell 70 is provided with a hollow bead 72, as seen in the transverse cross-sectional view of FIG. 5. The shell 70 is comparable to shell 26 with the exception of the hollow bead construction. This bead 72 has a tubular hollow region 74 running along the entire length of the bead 72, considering the bead length running round the circumference of the side edge of the shell 70. This hollow bead 72 reduces the rigidity of the shell 70, at the interface with the membrane 38, in comparison to the shell with a solid bead of the same diameter (as shown in FIG. 4). By reducing the rigidity of the shell 70 at the bead 72, where the shell 70 interacts with the membrane 38, the shell 70 deforms more during the inflation-deflation cycle (as compared to a shell with a solid bead), thereby allowing the shell 70 to share with the membrane 38 more of the stress caused by the cycling. It will be appreciated that if the shell is very rigid relative to the membrane (for example if it has a large-diameter solid bead), the membrane 38 is forced to absorb a greater share of the stress related to the cycling of the pump.

Figure 6:
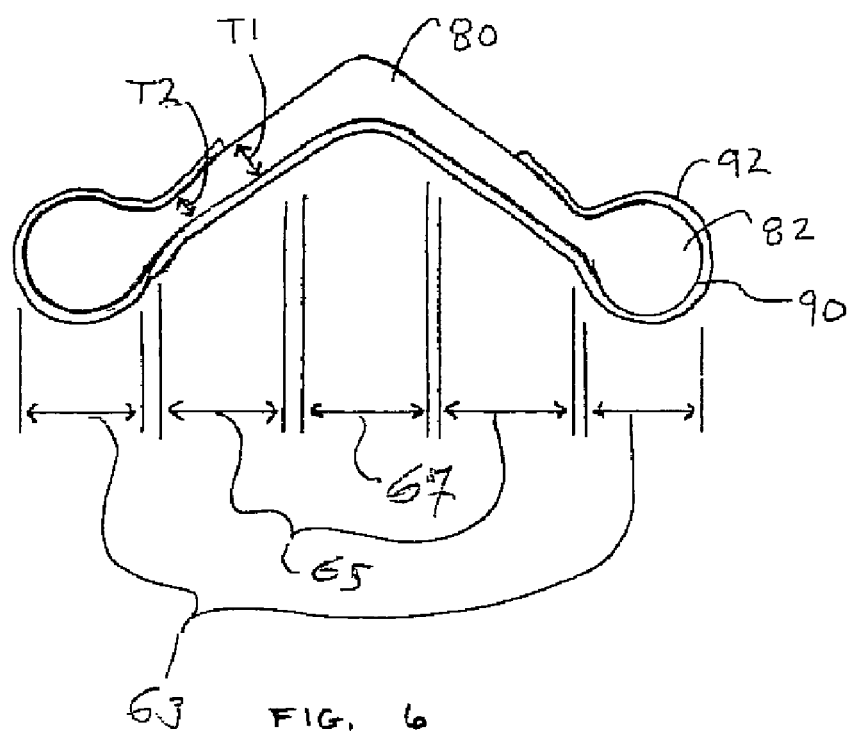
FIG. 6 is a schematic view of a transverse planar cross-sectional view of a blood pump in a deflated state, in an embodiment with the shell's wall region decreasing in thickess adjacent to the bead.

The thickness of the wall region 86 of the inventive shell 80 decreases from a maximum near the spine region 67 to a minimum near the bead region 63, so that T1 is greater than T2, as seen in the transverse cross-sectional view of FIG. 6. The thinner wall region T2 decreases rigidity of the shell 80 at the bead region 63 and consequently at the bead membrane contacting region 90 with the membrane 38, in comparison to the shell 70 with a wall region of uniform thickness (as shown in FIG. 5). By reducing the rigidity of the shell 80 at the bead region 63, where the shell 80 interacts with the membrane 38, the shell 80 deforms more during the inflation-deflation cycle (as compared to a shell with a wall region of uniform thickness), thereby allowing the shell 80 to share more of the stress caused by the cycling with the membrane 38.

In yet another embodiment, the membrane is modified, as compared to known pump membranes, to enhance the durability of the blood pump. In particular, the membrane 38 is preferably formed such that even without an applied pressure or vacuum (that is, without any significant pressure differential from one side of the membrane to the other), membrane shape generally matches that of the curved inner surface 31 of the shell 26, as seen in FIG. 2. This curved membrane is formed on a curved surface. This curved membrane experiences less creasing during the inflation-deflation cycles, as compared to flat membranes. Practical experience has shown that flat membranes crease at certain cusp points on the curved shell when they transition between inflated and deflated states. Analysis and testing indicate that the curved membrane reduces the magnitude and occurrence of this creasing problem.

Figure 7:
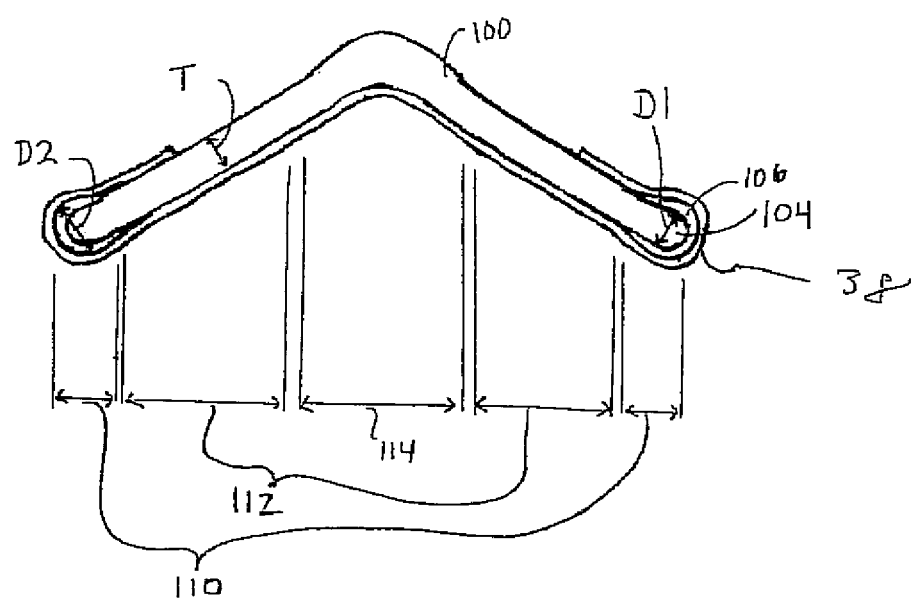
FIG. 7 is a schematic view of a transverse cross-sectional view of a blood pump in a deflated state, in an embodiment view with an air pocket between the membrane and the bead.

In another embodiment, the blood pump is provided with an air pocket between the membrane and the bead, when the blood pump is in a deflated state, to reduce the stress on the membrane during the cyclical operation of the pump. As seen in the transverse cross-sectional view of the pump in FIG. 4A, the bead has a membrane-contacting region 69 which typically contacts the portion of the membrane when the pump is deflated. As shown in FIG. 7, membrane 102 does not contact the bead 104 around the entire cross-sectional diameter of the bead 104, due to air pockets 106 which form in proximity to the bead 104 during the deflation cycle. By heat setting the membrane on a large bead shell forming platen, and then bonding the resulting membrane 102 to shell 100 with a relatively smaller bead 104, during deflation, the diameter D2 of the air pocket created by the membrane 102 wrapping around the bead 104 is larger than the diameter D1 of the bead 104. In order to further reduce localized stresses on the membrane 102 during the deflation cycle, the diameter D2 of the air pocket 106 created by the membrane 102 is always greater than the bead diameter D1. In other words, D2>D1. The local diameter D1 of the bead 104 in this embodiment is preferably between about 110% to about 700% of the wall thickness T. In other words, $\approx 1.1\ T \leq D1 \leq \approx 7\ T$. More preferably, D1 is between about 110% to about 300% of T. In other words, $\approx 1.1\ T \leq D1 \leq \approx 3\ T$. An air pocket 106 is formed in the gap between the membrane 102 and the bead 104. The air pocket increases the radius of curvature of the membrane 102 near the bead 104, thus reducing the strain on the membrane 102 during inflation-deflation cycles.

As best seen in FIGS. 12-15, a shell 326 is relatively flat along a shell length with slightly downturned ends at the longitudinal termini, and a general cylindrical shape, with an upper or outer surface 339 that is convex in both longitudinal and transverse extents. The lower or inner surface 331 of the shell 326 is concave in its longitudinal and transverse extents.

The shell 326 can be considered as having three regions: the spine region 357, the wall region 355, and the bead region 353. The spine region 357 of the shell 326 is the relatively thick area of the shell that forms the housing 341 around the hose barb 340, together with the area immediately surrounding the housing 341. A passage 328 extends though the shell 326 to place the interior volume 330 of the blood pump 320 in fluid communication with the conduit 332 of the blood pump 20.

Figure 14:
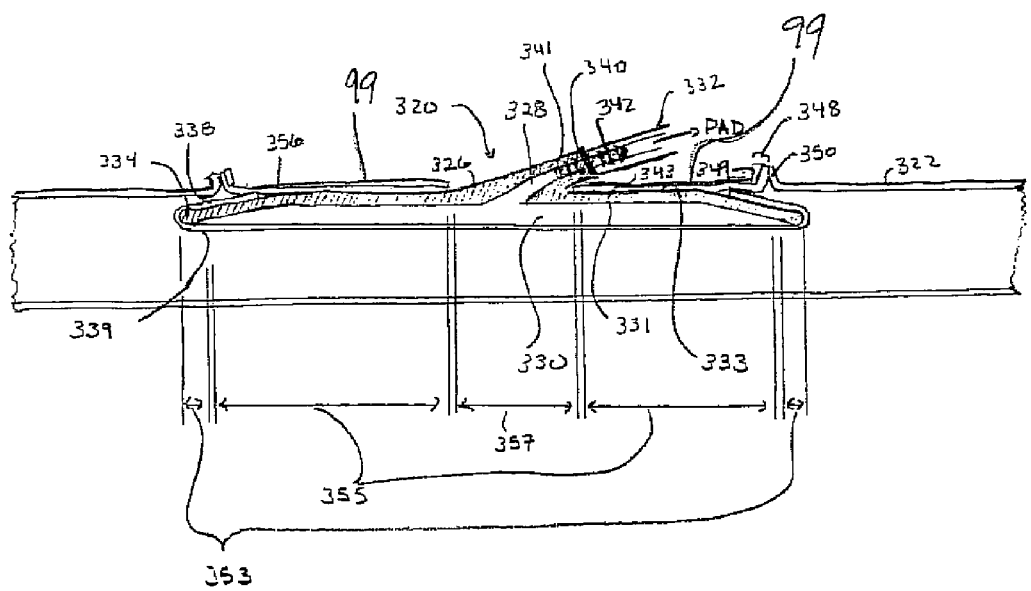
FIG. 14 is a schematic view of a longitudinal cross-sectional view of a cylindrical blood pump with no vacuum/pressure applied to the membrane.

The wall region 355 of the shell 326 is preferably thinner than the spine region 357 and extends out from the spine region 357 as seen in FIG. 14.

Figure 15:
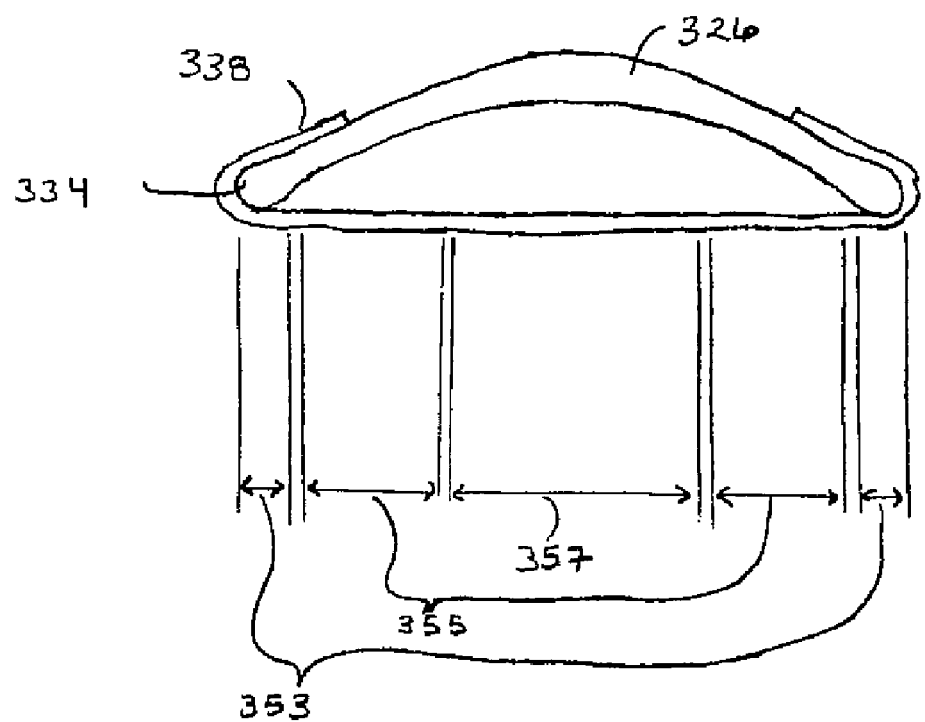
FIG. 15 is a schematic view of a transverse cross-sectional view of a cylindrical blood pump with no vacuum/pressure applied to the membrane.

The bead region 353 of the shell 326 has a bead 334, and is thicker than the wall region 355. The bead 334 extends around the periphery of the shell 326, as best seen in FIGS. 14 and 15. The bead 334 is smoothly rounded throughout its entire extent, circumferentially around the cylindrical, elliptical shell 326. The bead 334 minimizes local flexing stress, particularly when the membrane 338 is taut around the edge during the pump deflation cycle.

The membrane 338 is flexible, thin walled and is bonded to the outer surface 333 of the shell 326. The membrane 338 is preferably not adhered to the bead 334 and inner surface 331 of the shell 326. Known solvation bonding techniques such as chlorinated solvent welding of polymers result in the membrane 338 and the shell 326 becoming what is in effect a unitary structure, but for purposes of explanation, the membrane 338 and the shell 326 are drawn in FIGS. 14 and 15 as separate components.

The outer surface 339 of the membrane 338 which, when implanted, interfaces with the blood in the aorta is preferably provided with fibrils, forming a textured surface similar to a flocking, to promote cellular adhesion in forming a pseudo-intima on the outer surface 339 of the membrane 338.

A piece of sheet material 343 is attached to the outer surface 333 of the shell 326. As indicated in FIG. 14, the periphery of the material 343 is preferably not attached to the outer surface 333 of the shell 326 and projects freely from the shell 326 to create a flange 348. An additional material strip 349, such as a pledget strip, is sewn to the flange 348, to provide a suture ring 344 for implanting the device in an incision in the aorta, as best shown in FIG. 14. The strip 349 preferably has a fibrous surface allowing body tissues to migrate into, and mechanically interweaving with the strip 349, to augment the sealing action (initially established by surgical implantation sutures (not shown)) between the flange 348 of the suture ring 344 and the wall 50 of the aorta 22. The sheet material 343 and strip 349 are made of various appropriate materials, such as polyester, which are commercially available and have been certified for use in implanted devices.

At least two modifications are optionally made to increase the durability of this blood pump by reducing the physical wear and stress on the membrane. The membrane failure of prior art designs is understood to have often been caused by microperforations due to membrane deformation, or "creasing," during inflation-deflation cycles. This embodiment has a flat membrane 338 which lies flat and parallel to the plane described by the bead 334 of the shell 326, when no pressure/vacuum is applied to the membrane 338, as best seen in FIGS. 14 and 15. The shell 326 has a general cylindrical shape with an interior surface area that is generally planar if the cylinder were "unrolled." The surface area of the flat membrane 338 is complementary to the interior surface area of the cylindrical shell, and thus, the creasing at cusp points that is known to occur with a flat membrane and a curved shell at cusp is greatly reduced in this embodiment, resulting in increased membrane and pump durability. Further, this embodiment has improvements to decrease the occurrence of deformation during implantation. The cylindrical shell 326 includes a spine region, the relatively thicker region near the hose barb housing, which adds structural strength to the pump and decreases the likelihood of deformation during implantation; such deformations resulted in membrane creasing in prior art pumps.

As seen in FIGS. 2, 3, 10 and 14, the pump 26 or 326 is constructed so that the suture ring 44 and its flange 48 are located proximally closer to the spine region 57 of the shell 26, as compared to prior art pumps. The suture ring 44 or 344 is located inward of the peripheral side edge 31 or 331 of the shell 26 or 326 viewed from above (as in FIG. 10 for shell 26): when the pump is viewed from the side, as in FIG. 2 or 14, the suture ring 44 or 344 is seen as being located above the outer surface 33 or 333, as well as being entirely located between the longitudinal ends of the shell 26 or 326.

Figure 11:
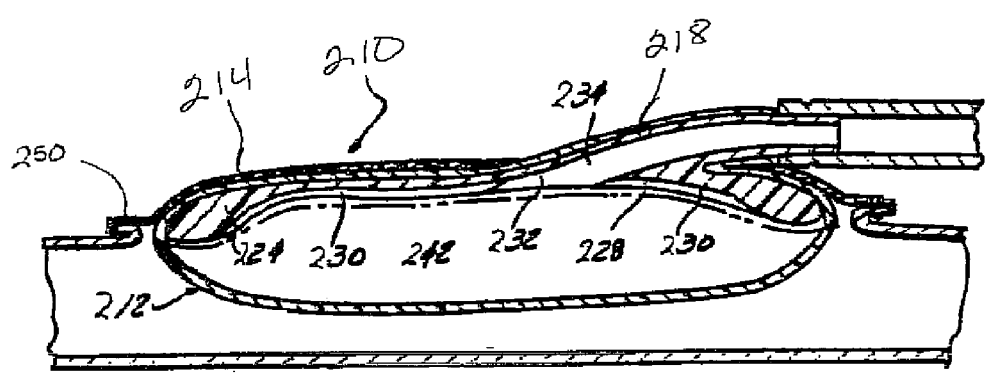
FIG. 11 is a longitudinal cross-sectional view of a prior art blood pump shell.
Figure 12:
FIG. 12 is a perspective view of a cylindrical blood pump shell, including a hose barb.
Figure 13:
FIG. 13 is a longitudinal cross-sectional view of a cylindrical blood pump shell, including a hose barb.

In prior art designs, as seen in FIG. 11, the flange 250 of the suture ring 214 is located adjacent to, and "outboard" of the bead 224 of the shell, resulting in the suture ring and the eventual incision scar interfering with the flexing of the shell, effectively increasing the rigidity of the shell. The improved suture ring placement of the present invention prevents the suture ring itself, as well as scar tissue forming on the suture ring, from interfering with the flexing of the shell during the inflation-deflation cycles, a design flaw found in prior art designs, as seen in FIG. 11.

In order to facilitate surgical explantation of the device, the outer surface 56 or 356 of the sheet material 43 or 343, other than at the flange 48 or 348, is optionally overlaid with a substance to which tissue does not adhere. Biocompatible substances prohibiting cellular adhesion include fluoropolymers and silicone. The overlayer 99 prevents scar tissue from adhering to the sheet material 43, so the blood pump can be explanted if desired. Without the overlayer 99, as the implant incision healed, scar tissue would also adhere to the sheet material 43 covering the back of the blood pump complicating explantation of the pump 20 or 320.

In certain embodiments, the conduit 32 of the pump is connected to a hose barb 40 or 340, as seen in FIGS. 2, 3 and 14. The hose barb 40 or 340 is preferably molded into the outer surface 33 or 333 of the shell 26 or 326. The hose barb is of rigid biocompatible, nonferrous, MRI-compatible material, such as titanium. The conduit 32 or 332 connects to the hose barb 40 or 340 and runs to the PAD (not shown). The passage 42 or 342 through the hose barb 40 or 340 connects to the passage 28 or 326 and places the interior volume 30 or 330 in fluid communication with the conduit 32 or 332.

While it is apparent that the illustrative embodiments of the invention herein disclosed fulfill the objectives stated above, it will be appreciated that numerous modifications and other embodiments may be devised by those skilled in the art. For example, it will be appreciated that features of the embodiments disclosed above can be used in various combinations and permutations. Therefore, it will be understood that the appended claims are intended to cover the forgoing—and all other—modifications and embodiments which come within the spirit and scope of the present invention.

The invention claimed is:

1. A blood pump, for placement in an incision in an aorta such that part of the pump after placement is in contact with blood passing through the aorta and being inflated and deflated to provide left ventricular assistance, the pump comprising:

an elongate shell having a generally elliptical shape, an outer shell surface which is convex, an inner shell surface which is concave, with a peripheral side edge located between the outer shell surface and the inner shell surface and terminating in a bead edge, and a passage in fluid communication between the outer shell surface and the inner shell surface;

an airtight membrane having an inner membrane surface facing the inner shell surface and an outer membrane surface facing away from said shell; and a membrane edge bonded to said shell along a region of the outer shell surface adjacent to the bead edge to form an enclosed internal chamber in fluid communication with said passage, said membrane edge looped with a maximum linear span of curvature that is greater than a maximal transverse linear extent of said bead edge.

2. The blood pump of claim 1, further comprising a hose barb molded into said shell, the hose barb having a longitudinal bore in fluid communication with said passage and a conduit-connecting portion extending outwardly from the outer shell surface, and adapted to connect to a fluid conduit.

3. The blood pump of claim 2, wherein said hose barb is formed from titanium.

4. The blood pump of claim 1, further comprising a piece of sheet material having a first portion that is attached to the outer surface of said shell, and a second portion that is unattached to the outer surface of the shell, the unattached area forming a suture ring for attaching the pump to the aorta of a patient.

5. The blood pump of claim 4, further comprising an overlayer nonadherent to scar tissue on an exposed surface of said piece of sheet material.

6. The blood pump of claim 1, wherein the bead edge has a circular cross-sectional shape.

7. The blood pump of claim 1, wherein said shell is curved to generally match the contour of the aorta.

8. A blood pump, for placement in an incision in an aorta such that part of the pump after placement is in contact with blood passing through the aorta and being inflated and deflated to provide left ventricular assistance, the pump comprising:

an elongate shell having a generally elliptical shape, an outer shell surface which is convex, an inner shell surface which is concave, with a peripheral side edge located between the outer shell surface and the inner shell surface and terminating in a bead edge, and a passage in fluid communication between the outer shell surface and the inner shell surface;

an airtight membrane having an inner membrane surface facing the inner shell surface and an outer membrane surface facing away from said shell; and a membrane edge bonded to said shell along a region of the outer shell surface adjacent to the bead edge to form an enclosed internal chamber in fluid communication with said passage, wherein the bead edge has an internal hollow region.

9. A blood pump, for placement in an incision in an aorta such that part of the pump after placement is in contact with blood passing through the aorta and being inflated and deflated to provide left ventricular assistance, the pump comprising:

an elongate shell having a generally elliptical shape, an outer shell surface which is convex, an inner shell surface which is concave, with a peripheral side edge located between the outer shell surface and the inner shell surface and terminating in a bead edge, and a passage in fluid communication between the outer shell surface and the inner shell surface;

an airtight membrane having an inner membrane surface facing the inner shell surface and an outer membrane surface facing away from said shell; and a membrane edge bonded to said shell along a region of the outer shell surface adjacent to the bead edge to form an enclosed internal chamber in fluid communication with said passage, wherein the bead edge has an ellipsoidal cross-sectional shape.

10. A blood pump, for placement in an incision in an aorta such that part of the pump after placement is in contact with blood passing through the aorta and being inflated and deflated to provide left ventricular assistance, the pump comprising:

an elongate shell having a generally elliptical shape, an outer shell surface which is convex, an inner shell surface which is concave, with a peripheral side edge located between the outer shell surface and the inner shell surface and terminating in a bead edge having a maximal transverse linear extent between the outer shell surface and the inner shell surface, and a passage in fluid communication between the outer shell surface and the inner shell surface;

an airtight membrane having an inner membrane surface facing the inner shell surface and an outer membrane surface facing away from said shell; and a membrane edge looped with a maximal linear span of curvature that is greater than the maximal transverse linear extent with the edge bonding to said shell along a region of the outer shell surface adjacent to the bead edge forming an air pocket intermediate between the bead edge and said membrane during deflation of the blood pump.

11. The blood pump of claim 10, further comprising a hose barb molded into said shell, the hose barb having a longitudinal bore in fluid communication with said passage and a conduit-connecting portion extending outwardly from the outer shell surface, and adapted to connect to a fluid conduit.

12. The blood pump of claim 10, wherein the bead edge has an internal hollow region.

13. The blood pump of claim 10, wherein said shell has a wall thickness T near the bead edge, the bead edge has a membrane-contacting region with a maximal linear extent of the bead edge at the membrane-contacting region being between 1.1 T and 7 T.

14. The blood pump of claim 10, further comprising a piece of sheet material having a first portion that is attached to the outer surface of said shell, and a second portion that is unattached to the outer surface of the shell, the unattached area forming a suture ring for attaching the pump to the aorta of a patient.

15. The blood pump of claim 14, further comprising an overlayer nonadherent to scar tissue on an exposed surface of said piece of sheet material.

16. The blood pump of claim 10, wherein the bead edge has a circular cross-sectional shape.

* * * * *